US006533455B2

(12) United States Patent
Graumann et al.

(10) Patent No.: US 6,533,455 B2
(45) Date of Patent: Mar. 18, 2003

(54) METHOD FOR DETERMINING A COORDINATE TRANSFORMATION FOR USE IN NAVIGATING AN OBJECT

(75) Inventors: Rainer Graumann, Hoechstadt (DE); Matthias Mitschke, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/944,933

(22) Filed: Aug. 31, 2001

(65) Prior Publication Data

US 2002/0044631 A1 Apr. 18, 2002

(30) Foreign Application Priority Data

Aug. 31, 2000 (DE) .......................... 100 42 963
Aug. 2, 2001 (DE) .......................... 101 37 914

(51) Int. Cl.[7] .................................................. A61B 6/08
(52) U.S. Cl. ..................... 378/205; 378/207; 600/427; 600/429
(58) Field of Search .............................. 378/162, 205, 378/207; 600/130, 424, 417, 426, 427, 429

(56) References Cited

U.S. PATENT DOCUMENTS

| | | | | |
|---|---|---|---|---|
| 5,769,861 A | | 6/1998 | Vilsmeier | 606/130 |
| 5,792,147 A | | 8/1998 | Evans et al. | 606/130 |
| 5,822,396 A | | 10/1998 | Navab et al. | 378/207 |
| 6,026,315 A | * | 2/2000 | Lenz et al. | 600/426 |
| 6,285,902 B1 | * | 9/2001 | Kienzle et al. | 600/427 |
| 6,456,868 B2 | * | 9/2002 | Saito et al. | 600/429 |
| 6,466,815 B1 | * | 10/2002 | Saito et al. | 600/429 |
| 6,470,207 B1 | * | 10/2002 | Simon et al. | 600/426 |

FOREIGN PATENT DOCUMENTS

| | | |
|---|---|---|
| DE | 43 06 037 | 8/1994 |
| DE | 196 32 273 | 12/1998 |

OTHER PUBLICATIONS

"Recovering Projection Geometry: How A Cheap Camera Can Outperform An Expensive Stereo System," Mitscke et al, IEEE Computer Society Conference on Computer Vision and Pattern Recognition, Jun. 13–15, 2000, vol. 1, pp. 193–200.
"A New Technique For Fully Autonomous and Efficient 3D Robotics Hand/Eye Calibration," Tsai et al, IEEE Trans. on Robotics and Automation, vol. 5, No. 3, Jun. 1999, pp. 345–358.
"Hand–Eye Calibration Using Dual Quaternions," Daniilidis, The International Journal of Robotics Research, vol. 18, No. 3, Mar. 1999, pp. 286–298.
"3D Reconstruction From Projection Matrices In A C–Arm Based 3D–Angiography System," Navab et al, Proc. 1st Int. Confl on Medical Image Computing and Computer Assisted Intervention (MICCAI), 1998.

* cited by examiner

*Primary Examiner*—Drew A. Dunn
*Assistant Examiner*—Courtney Thomas
(74) *Attorney, Agent, or Firm*—Schiff Hardin & Waite

(57) ABSTRACT

In a method for determining a coordinate transformation between a coordinate system of a first object to be imaged by an X-ray apparatus and a coordinate system of a second object to be navigated relative to a first object, a transformation relationship is determined between a coordinate system of a position-acquisition system and the coordinate system of the first object by an offline calibration run, the position of the X-ray arm is determined while recording X-ray images of the first object, and the position of the second object is determined using the position-acquisition system.

7 Claims, 1 Drawing Sheet

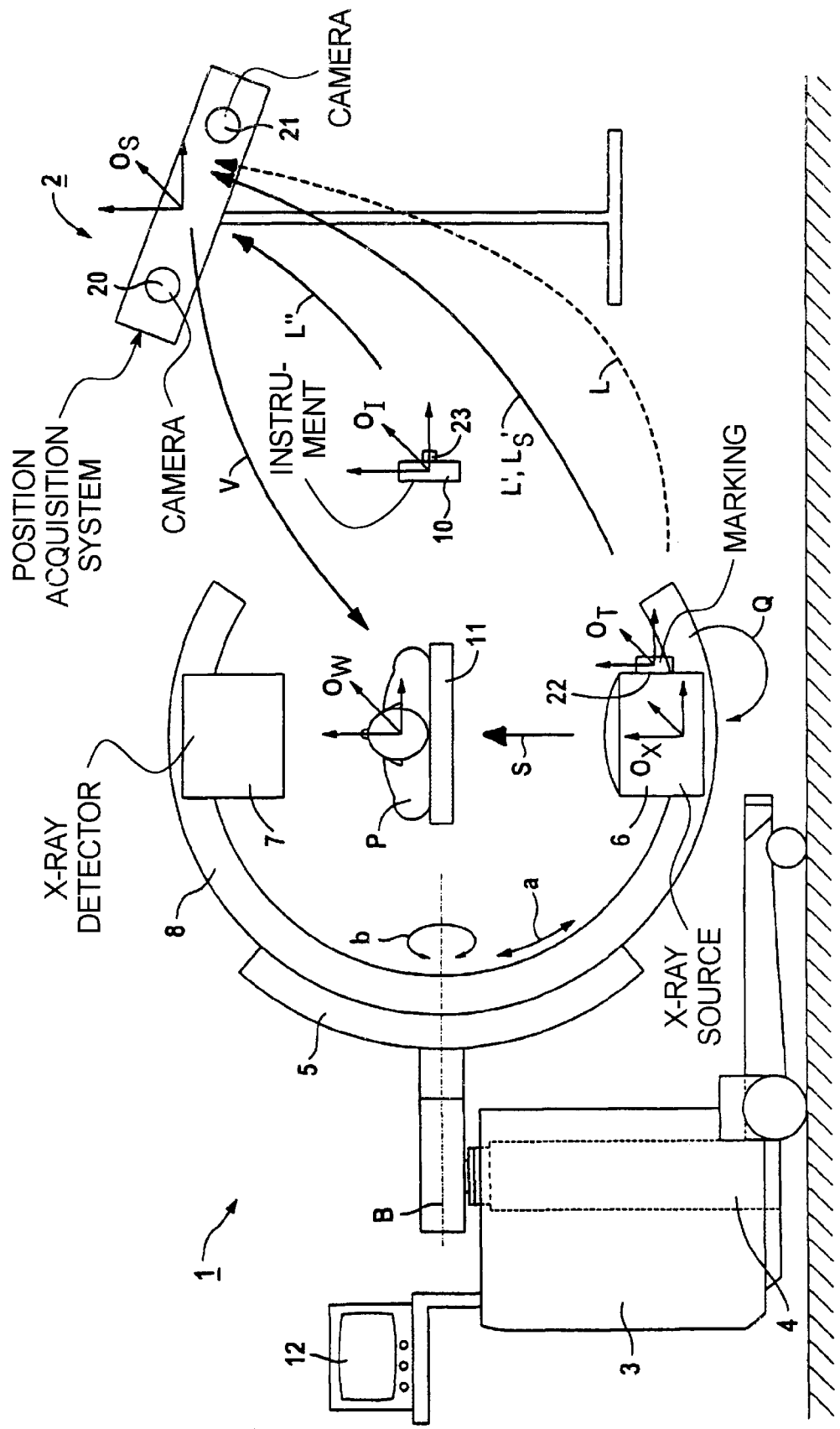

METHOD FOR DETERMINING A COORDINATE TRANSFORMATION FOR USE IN NAVIGATING AN OBJECT

BACKGROUND OF THE INVENTION

1. Field of the Invention

The present invention relates to a method for determining a coordinate transformation between a coordinate system of a first object to be imaged by an X-ray machine and a coordinate system of a second object to be navigated relative to the first object.

2. Description of the Prior Art

"Navigation" of a second object relative to a first object is generally defined as guiding the second object relative to the first object, aided by optical imaging information, where an image of the second object is inserted into imaging information on the first object obtained using the X-ray machine.

This type of procedure is becoming of increasing importance, particularly in the medical field, where, in the case of navigation-guided operations, an image of a medical instrument is usually inserted into recorded imaging information on a living being. This approach allows an operator to guide an instrument that has at least partially penetrated the living being and whose tip is no longer directly visible due to, for example, its having penetrated bodily tissue. Guidance is based on imaging information relative to that area of the tissue of the living being that is to be investigated or treated, without running the risk of inadvertently injuring the living being.

In order to allow such navigation-guided operations, i.e., to be able to insert an accurately positioned and accurately oriented image of the instrument into imaging information on a living being, it is necessary to generate a mathematical relationship in the form of a coordinate transformation between a coordinate system inscribed on the living being and a coordinate system of the instrument to be navigated. To that end, artificial markings are occasionally arranged on the living being or anatomical markings, for example, prominent bone structures, are established as references. The anatomical or artificial markings must be clearly visible in X-ray images of the living being and readily accessible on the living being. These artificial markings are, for example, attached to the surface of the skin of the living being, in order to allow their registration, which is defined as determining the rule for transforming the spatial coordinates defined for the coordinate system of the instrument to be navigated into the spatial coordinates of the living being to be employed for the navigation. The markings usually have to be individually accessed by the instrument in order to be able to determine the coordinate transformation between the coordinate system of the living being and the coordinate system of the instrument. The markings also are rigidly attached to the body of the living being in the case of high-precision medical procedures. Examples are the attachment of a stereotactile framework to a patient's head or the attachment of markings to a patient's bones or spinal column. The markings are sometimes attached in a separate operation, since they have to be attached prior to preoperative imaging, which is frequently employed for navigation purposes.

Attachment and registration of the markings is thus a relatively unpleasant procedure for a patient, as well as a relatively time-consuming procedure for an operator handling preparations for a navigation-guided operation.

A device and a method for computer-assisted surgery are known from DE 695 03 814 T2, corresponding to U.S. Pat. No. 5,792,147. In this case a particular light pattern is projected onto a location on a patient's body for which 3D-images have been previously obtained and archived. The light pattern is recorded by video cameras and employed for generating 3D-images of the light pattern. The archived 3D-images are superimposed on the 3D-images of the light pattern projected onto the surface of the patient's body in order to generate a common reference frame. The cameras also record a pattern that has an indicator that is inserted into the superimposed 3D-images for navigation purposes.

German OS 196 32 273 describes methods for determining the geometric parameters of a body that is free to move.

German OS 195 36 180, corresponding to U.S. Pat. No. 5,769,861 proposes rigidly attaching to a patient's body an internal marker fixture to establish an intracorporeal spatial reference system for localizing an instrument relative to three-dimensional data on the patient. The positions of three-dimensional data on the patient's body obtained from an analytical scan within the intracorporeal reference system established by the marker fixture are determined in conjunction with said analytical body scan. The location and orientation of the intracorporeal reference system established by the internal marker fixture relative to an extracorporeal reference system established by an external marker fixture are determined. The location and orientation of an instrument to be navigated in relation to the external marker fixture are determined, which allows a correlation to the internal marker fixture, and thus to the three-dimensional data on the patient's body, to be established.

A device and a method for correlating a center of intracardial activity that has been localized based on an electrocardiogram to an ultrasonic tomogram are known from German OS 43 06 037. This involves marking the location of a site of intracardial activity determined from an electrocardiogram on an ultrasonic tomogram with the aid of a position-acquisition system.

SUMMARY OF THE INVENTION

An object of the present invention to provide a method for determining a coordinate transformation between a coordinate system of a first object to be imaged by an X-ray machine and a coordinate system of a second object to be navigated relative to the first object that will eliminate the need for registration involving markings in order to define a relationship between the coordinate system of the first object and the coordinate system of the second object.

This object is inventively achieved in a method for determining a coordinate transformation between a coordinate system of a first object to be imaged by an X-ray apparatus and a coordinate system of a second object to be navigated relative to the first object, where a position-acquisition system for determining the positions of the X-ray apparatus and the second object is available, having the following method steps:

a) determining the transformation relationships L, V, and S between coordinate systems of the position-acquisition system, the X-ray apparatus, and the first object in a calibration run prior to obtaining imaging information from the first object using the X-ray apparatus, L being the coordinate transformation between a coordinate system of a marking arranged on said X-ray apparatus that interacts with the position-acquisition system and the coordinate system of the position-acquisition system, V being the coordinate transformation between the coordinate system of the position-acquisition system and the coordinate system of the first object, and S being the coordinate transformation between the coordinate system of the marking for a reference position of the X-ray apparatus relative to the first object and the coordinate system of the first object, b) determining the modified coordinate transformation L' between the coordinate system of the marking and the coordinate system of the position-acquisition system resulting from an altered position of the X-ray apparatus and the position-acquisition system relative to one another while obtaining imaging information from the first object using the X-ray apparatus, compared to the calibration run, or determining the modified coordinate transformation $L_S'$ between the coordinate system of the marking and the coordinate system of the position-acquisition system for the reference position of the X-ray apparatus relative to the first object while obtaining imaging information from the first object using the X-ray apparatus compared to the calibration run, c) determining the coordinate transformation L" between the coordinate system of the second object and the coordinate system of the position-acquisition system, and d) determining the coordinate transformation between the coordinate system of the second object and the coordinate system of the first object based on the coordinate transformations V, L, L', $L_S'$, L", and S determined in steps a) through c).

According to the invention, a transformation relationship between the coordinate system of a first object and the coordinate system of a second object employed for navigating said second object relative to the first object is derived by determining coordinate transformations between the items of equipment involved in the imaging and the objects alone, without having to perform any registrations involving markings.

In an embodiment of the present invention an image of the second object obtained using a C-arm X-ray apparatus is inserted into a 3D-image of the first object for navigation purposes. Various 3D-images may be obtained from a series of 2D-projections taken at different projection angles of the X-ray system of said C-arm X-ray apparatus relative to the first object. Knowledge of the projection geometries involved, expressed in terms of "projection matrices" determined from a single calibration procedure performed with the aid of an X-ray calibration phantom for the employed X-ray apparatus, prior to undertaking measurements on patients, is required. The coordinate transformations L, V, and S mentioned above are determined during this calibration procedure. Determining the projection matrices and determining the coordinate transformations L, V, and S is described in detail in the article by M. Mitschke and N. Navab entitled "Recovering Projection Geometry: How a cheap camera can outperform an expensive stereo system," IEEE Computer Science Conference on Computer Vision and Pattern Recognition, Jun. 13–15, 2000, Hilton Head Island, S.C. Volume 1, pp. 193–200, the teachings of which are incorporated herein by reference.

Finally, the coordinate transformation between the coordinate system of the second object and the coordinate system of the first object is determined, based on the coordinate transformations L, V, and S determined from the calibration run using the coordinate transformations, L', $L_S'$, and L", determined while obtaining imaging information from the first object with the position-acquisition system.

In another embodiment of the present invention a coordinate transformation M is determined from the coordinate transformations L and L' employing the relationship $M=L'L^{-1}$, which expresses the variation in the transformation relationship between the coordinate system of the marking arranged on the X-ray apparatus and the coordinate system of the position-acquisition system. This change is due to the fact that the position-acquisition system and the X-ray apparatus usually have different positions and orientations relative to one another during navigation-guided operations than during calibration. According to a variant of the present invention, the coordinate transformation between the coordinate system of the second object and the coordinate system of the first object may thus be expressed in terms of the relationship V M L".

In another embodiment of the present invention, the coordinate transformation between the coordinate system of the second object and the coordinate system of said first object are expressed in terms of the relationship $S L_S'^{-1} L"$, where the coordinate transformation $L_S'$ has been determined for the reference position of the X-ray apparatus relative to the first object during acquisition of X-ray images of the first object with the position-acquisition system.

DESCRIPTION OF THE DRAWINGS

The FIGURE is a schematic illustration of an exemplary embodiment of the present invention, showing the transformation relationships between the individual coordinate systems of an X-ray apparatus, a position-acquisition system, and first and second objects.

DESCRIPTION OF THE PREFERRED EMBODIMENTS

The FIGURE depicts a C-arm X-ray apparatus 1 and a position-acquisition system 2.

The C-arm X-ray apparatus 1 has an equipment cart 3 with a lifting mechanism 4 connected to a bearing part 5. Mounted on the bearing part 5 is a C-shaped arc 8 equipped with an X-ray source 6 and an X-ray detector 7, which, in the case of the exemplary embodiment shown here, is isocentrically variable over its circumference (cf. double-ended arrow a). The C-shaped arc 8, along with the bearing part 5, is also isocentrically pivotable about its radial axis B, in the case of the example shown here, in the directions indicated by the double-ended arrow b.

The C-arm X-ray apparatus 1 allows 2D-images and 3D-images of a patient P (schematically depicted) supported on a bed 11 to be acquired and displayed on a display device 12. The equipment required for this, in particular an image-processor, is constructed in a known manner, and thus does not appear in the FIGURE and is not explicitly described herein.

The position-acquisition system 2 of the exemplary embodiment is an optical position-acquisition system equipped with a camera system having two cameras 20 and 21 in the exemplary embodiment, a marker plate 22 arranged on the X-ray source 6, and a marker 23 arranged on a medical instrument 10. The position-acquisition system 2 allows the positions and orientations of the marker plate 22, and thus of the X-ray system consisting of the X-ray source 6 and said X-ray detector 7, as well as the positions and orientations of the marker 23, and thus of the instrument 10 to be determined.

The computing equipment of the position-acquisition system, for example, a commercially available computer, needed for determining the positions, is constructed in a known manner, and thus does not appear in the FIGURE and is not explicitly described herein.

The position-acquisition system 2 allows navigation-guided operations on a patient P to be performed in which an operator (not shown in the FIGURE) guides the instrument 10 relative to the patient P, based on, for example, imaging information from the patient P displayed on the display device 12 into which an image of the instrument 10 has been inserted. In the exemplary embodiment, the imaging information from the patient P employed for the navigation-guided operation is obtained intraoperatively, i.e., during a medical operation on the patient P, using the C-arm X-ray apparatus 1.

However, knowledge of the coordinate transformation between a coordinate system $O_W$ inscribed on said patient P and a coordinate system $O_I$ inscribed on the instrument 10, whose determination of which in accordance with the present invention is described below, is required in order to be able to perform a navigation-guided operation.

The coordinate system $O_X$ is inscribed on the X-ray system or X-ray source 6, the coordinate system $O_S$ is inscribed on the camera system of the position-acquisition system 2, and the coordinate system $O_T$ is inscribed on the marker plate 22 arranged on the X-ray source 6. Although all of these coordinate systems are represented as Cartesian coordinate systems in the FIGURE, this need not be the case. Furthermore, the choice of the location and orientation of the coordinate systems, along with their designations, are only exemplary.

Since the navigation involved preferably employs 3D-imaging information from the patient P obtained intraoperatively using the C-arm X-ray apparatus 1, in an initial stage, the projection geometries of said C-arm X-ray apparatus 1 are determined in the form of "projection matrices" using an X-ray calibration phantom, usually under a single calibration procedure conducted offline, i.e., prior to the conduct of measurements from the patient P. An, X-ray calibration phantom suitable for this purpose is known from, for example, U.S. Pat. No. 5,822,396.

3D-images of an object, the patient P in the exemplary embodiment, may be generated from a series of 2D-projections obtained using the C-shaped X-ray apparatus 1 using the projection geometries obtained from the offline calibration procedure. In the course of determining the projection geometries, the coordinate transformations L, Q, V, and S will be determined in the offline calibration procedure. L is the coordinate transformation between the coordinate system $O_T$ of the marker plate 22 belonging to the position-acquisition system 2 that is arranged on the X-ray source 6 and the coordinate system $O_S$ of the camera system of the position-acquisition system 2. Q is the coordinate transformation between the coordinate system $O_T$ of the marker plate 22 and the coordinate system $O_X$ of the X-ray system. V is the coordinate transformation between the coordinate system $O_S$ of the position-acquisition system 2 and the coordinate system $O_W$ of the patient P or that employed during the calibration of the X-ray calibration phantom. S is the coordinate transformation between the coordinate system $O_T$ of the marker plate 22 for a reference position of the C-shaped arc 8 relative to the calibration phantom and the coordinate system $O_W$ of the patient P or that employed during the calibration of the X-ray calibration phantom. The reference position of the C-shaped arc 8 can be, for example, the position for which the initial 2D-projection of a series of 2D-projections employed for obtaining a 3D-image of the calibration phantom or the patient P is recorded. The coordinate transformation L is indicated in the FIGURE by dotted lines, since, for the situation shown in the FIGURE, i.e., measuring a patient, this coordination transformation usually differs from that for the situation that applies during the offline calibration. The differences involved are due to an altered position and orientation of the C-arm X-ray apparatus 1 and the resultant altered positions of the marker plate 22 and the camera system of said position-acquisition system 2 relative to one another compared to the offline calibration.

Both the projection matrices for the 3D-imaging and the coordinate transformations L, Q, V, and S will ne known from the offline calibration. These are determined as described in detail in the article by M. Mitschke and N. Navab entitled "Recovering Projection Geometry: How a cheap camera can outperform an expensive stereo system," IEEE Computer Science Conference on Computer Vision and Pattern Recognition, Jun. 13–15 2000, Hilton Head Island, S.C. Volume 1, pp. 193–200, the teachings of which are incorporated herein by reference. In the exemplary embodiment, the projection geometries and the coordinate transformations are determined using the image-processor of the C-arm X-ray apparatus 1 and the Computer of the position-acquisition system 2, which interact with one another. The projection matrices and the coordinate transformations L, Q, V, and S are stored in a memory (not shown in the FIGURE) of said C-arm X-ray apparatus 1 for later use in reconstructing 3D-images of an object and for navigation purposes.

A series of 2D-projections of the patient P is recorded from various projection angles while measuring said patient P, i.e., while obtaining 3D-images of the patient P using the C-arm X-ray apparatus 1, with the C-shaped arc 8 and the camera system having different positions relative to one another than during offline calibration. The positions of the C-shaped arc 8, from which the coordinate transformation L' resulting from the altered position of the C-shaped arc 8 and the camera system relative to one another are derived, is determined by the position-acquisition system 2. Finally, the changes in the position and orientation of the marker plate 22, compared to those for the offline calibration determined from said original coordinate transformation L and the coordinate transformation L' determined during measurements from said patient P, may be described by the additional coordinate transformation M. The coordinate transformation M follows from the relationship M L=L' by $L^{-1}$ as $M=L'L^{-1}$.

The transformation relationship between the coordinate system $O_S$ of the camera system of the position-acquisition system 2 and the coordinate system $O_W$ of the patient P during navigation-guided operation is then known. The position and orientation of the instrument 10 is determined with the marker 23 and the camera system of the position-acquisition system 2, with the coordinate transformation from the coordinate system $O_I$ of said medical instrument 10 to be navigated to the coordinate system $O_S$ of the camera system of the position-acquisition system 2 being designated by L". The position and orientation of the medical instrument 10 tracked by the position-acquisition system 2 relative to a reconstructed volume of the patient P shown on a 3D-image thus can be immediately determined. The coordinate transformation between the coordinate system $O_I$ of the instrument and the coordinate system $O_W$ of the patient P then becomes V M L". Finally, an image of the instrument 10 accurately depicting its position and orientation is inserted into the reconstructed volume of the patient P appearing on said display device 12, based on the coordinate transformation.

A second variant of the method for determining the coordinate transformation between the coordinate system $O_I$ of the instrument 10 and the coordinate system $O_W$ of the patient P results from employing the coordinate transformation, S. However, said coordinate transformation $L_S'$ is determined by the position-acquisition system 2 for the same reference position of the C-shaped arc 8 for which the coordinate transformation S was determined, due to the differing position of the C-shaped arc 8 relative to the camera system of the position-acquisition system 2 during measurements on said patient P compared to offline calibration. The relation between the coordinate system $O_S$ of the camera system of the position-acquisition system 2 and said coordinate system $O_W$ of the patient P is then known in this case as well, so that the coordinate transformation from the coordinate system $O_I$ of the instrument 10 to the coordinate system $O_W$ of the patient P also be computed using the coordinate transformation L". In this case the transformation rule $S L_S'^{-1} L''$.

This makes it clear that determining the coordinate transformations L, V, and S via an offline calibration run and determining the coordinate transformations L" or $L_S'$ and L" intraoperatively, i.e., during measurements on a patient, alone will be sufficient to allow the transformation relationship to be determined between the coordinate system $O_W$ of the patient P and the coordinate system $O_I$ of the instrument 10 needed to allow navigating the instrument 10 relative to the patient P. The present invention thus eliminates need for registrations involving markings.

Furthermore, the position-acquisition system employed for navigation need not be an optical position-acquisition system. Electromagnetic or other known types of position-acquisition systems may alternatively be employed.

The directions of the coordinate transformations shown in the FIGURE are only exemplary. The important feature is the determination of a coordinate transformation between two coordinate systems.

The invention was described above with reference to the example of a medical application, however, the application of the invention is not limited to the field of medicine.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining a coordinate transformation between a coordinate system of a first object and a coordinate system of a second object to be navigated relative to said first object, comprising the steps of:

providing a position acquisition system having a coordinate system associated therewith;

providing an X-ray apparatus for obtaining an X-ray image of said first object;

providing a marking on said X-ray apparatus detectable by said position acquisition system, said marking having a coordinate system associated therewith;

executing a calibration run prior to obtaining said X-ray image;

in said calibration run, determining a coordinate transformation L between the coordinate system of said marking and the coordinate system of said position acquisition system, and a coordinate transformation V between the coordinate system of said position acquisition system and the coordinate system of said first object;

determining a modified coordinate transformation L' between said coordinate system of said marking and said coordinate system of said position acquisition system resulting from an altered position of said X-ray apparatus and said position acquisition system relative to each other while obtaining said X-ray image of said first object using said X-ray apparatus;

determining a coordinate transformation L" between the coordinate system of the second object and the coordinate system of the position acquisition system; and determining a coordinate transformation between said coordinate system of said second object and the coordinate system of said first object using said coordinate transformations V, L, L' and L".

2. A method as claimed in claim 1 comprising determining a coordinate transformation M from said coordinate transformations L and L' according to the relationship $M = L'L^{-1}$.

3. A method as claimed in claim 2 comprising determining said coordinate transformation between the coordinate system of said second object and the coordinate system of said first object by VML".

4. A method as claimed in claim 1 comprising employing a C-arm X-ray apparatus as said X-ray apparatus.

5. A method for determining a coordinate transformation between a coordinate system of a first object and a coordinate system of a second object to be navigated relative to said first object, comprising the steps of:

providing a position acquisition system having a coordinate system associated therewith;

providing an X-ray apparatus for obtaining an X-ray image of said first object;

providing a marking on said X-ray apparatus detectable by said position acquisition system, said marking having a coordinate system associated therewith;

executing a calibration run prior to obtaining said X-ray image, including placing said X-ray apparatus in a reference position relative to said first object;

in said calibration run, determining a coordinate transformation S between the coordinate system of said marking, when said X-ray apparatus is in said reference position, and the coordinate system of said first object;

determining a coordinate transformation $L_S'$ between the coordinate system of said marking at said reference position of said X-ray apparatus and the coordinate system of said position acquisition system while obtaining said X-ray image of said first object;

determining a coordinate transformation L" between the coordinate system of the second object and the coordinate system of the position acquisition system; and determining a coordinate transformation between said coordinate system of said second object and the coordinate system of said first object using said coordinate transformations $L_S'$, L" and S.

6. A method as claimed in claim 5 comprising determining said coordinate transformation between the coordinate system of said second object and the coordinate system of said first object by $SL_S'^{-1}L''$.

7. A method as claimed in claim 5 comprising employing a C-arm X-ray apparatus as said X-ray apparatus.

* * * * *